United States Patent [19]

Matsumura et al.

[11] Patent Number: 4,957,614

[45] Date of Patent: Sep. 18, 1990

[54] ELECTROCHEMICAL DETECTION DEVICE

[75] Inventors: Hideo Matsumura, Nara; Hirohito Nishino, Kusatsu; Hidetoshi Fukuyama, Joyo; Kazutoshi Yamazaki, Otsu; Hiromitsu Suzuki, Ibaraki, all of Japan

[73] Assignee: Sekisui Kagaku Kogyo Kabushiki Kaisha, Osaka, Japan

[21] Appl. No.: 157,564

[22] Filed: Feb. 19, 1988

[30] Foreign Application Priority Data

Feb. 20, 1987 [JP] Japan ............................... 62-24833[U]
Feb. 20, 1987 [JP] Japan ................................... 62-40531

[51] Int. Cl.⁵ ........................................... G01N 27/28
[52] U.S. Cl. ..................................... 204/411; 204/409
[58] Field of Search .............. 204/402, 409, 411, 412, 204/408; 422/68, 81

[56] References Cited

U.S. PATENT DOCUMENTS

| | | | |
|---|---|---|---|
| 3,505,195 | 4/1970 | Nielsen et al. | 204/415 X |
| 3,575,836 | 4/1971 | Sternberg | 204/415 |
| 4,059,406 | 11/1977 | Fleet | 204/412 X |
| 4,083,766 | 4/1978 | Landon et al. | 204/412 X |
| 4,172,770 | 10/1979 | Semersky et al. | 204/412 X |
| 4,376,681 | 3/1983 | Inoue et al. | 204/415 X |
| 4,397,725 | 8/1983 | Enzer et al. | 204/406 |
| 4,596,649 | 6/1986 | Hofmeier et al. | 204/411 |

FOREIGN PATENT DOCUMENTS 3242456 5/1984 Fed. Rep. of Germany .

OTHER PUBLICATIONS

Patent Abstracts of Japan, vol. 5, No. 100.

Primary Examiner—Nam X. Nguyen
Attorney, Agent, or Firm—Armstrong, Nikaido, Marmelstein, Kubovcik & Murray

[57] ABSTRACT

An electrochemical detection device comprising a cell unit that has a cell therein and a supporter that rotatably supports said cell unit and that is made in one piece with said cell unit, wherein said cell unit has a cell block that has a test solution introduction route through which a test solution flows after being introduced into the inside of said cell block and that has a test solution outlet route through which the test solution leaves the inside and that has a reference electrode and a counter electrode provided so that they come into contact with the test solution flowing from said test solution introduction route to said test solution outlet route; a gasket that has an opening constituting said cell, and that is in contact with said cell block so that said opening is connected with both the test solution introduction route and the test solution outlet route; a working electrode that faces said opening of the gasket, and said supporter has a pressure means that pushes said working electrode onto said cell block by means of said gasket while said supporter and said cell unit are being incorporated into one piece, which removes the pressure from said pressure means.

9 Claims, 5 Drawing Sheets

ELECTROCHEMICAL DETECTION DEVICE

BACKGROUND OF THE INVENTION

1. Field of the invention:

This invention relates to an electrochemical detection device that electrochemically measures specific substances in a test solution. More particular, this invention relates to an electrochemical detection device in which the working electrode can be readily installed in and from which the working electrode can be readily removed by a simple operation.

2. Description of the prior art:

Electrochemical detection devices have a cell through which a test solution can pass, and a working electrode and a counter electrode that apply a given voltage to the test solution within the said cell. The working electrode and counter electrode apply voltage to the test solution within the cell, resulting in an electrochemical reaction by which the amount of specific substance in the test solution is measured. Ordinarily, the cell mentioned above is formed of a cell block. Each of the electrodes is formed so as to have a given shape and size, and they are introduced into said cell block and fixed by means of a screw or the like. The electrodes are connected electrically to measuring devices on the outside.

These kinds of electrochemical detection devices have been used in recent years to assay the amounts of catecholamines or other kinds of biochemicals in test samples. Test solutions that contain such kinds of biochemicals state the electrodes and the cell wall. In particular, the working electrode is readily stained by test solutions. Staining of the inside of the cell and of the electrodes decreases the accuracy of the measurements. For this reason, it is necessary to clean the inside of the cell and the electrodes. The inside of the cell is cleaned by the opening of the cell. Conventional cells are made into the one unit by the screwing together, etc., of elements of the structure of the cell. For this reason, in order to open the cell, the structural elements of the cell must be taken apart, and after the inside of the cell has been cleaned, it is necessary to reassemble the structural elements, which requires a great deal of work.

When the electrodes, also, are to be cleaned, it is necessary that the electrodes be released from the cell block. Also, when the sample to be assayed in an electrochemical detection devices is changed, it is necessary to replace the electrodes with different ones. In this circumstance, too, the electrodes that are fixed with screws or the like to the cell block must be temporarily removed from the cell block. When the electrodes are being exchanged, first the electrical connections between the electrodes and the fixed measurement devices must be removed, and then different electrodes must be fixed to the measurement devices, after which it is necessary to restore the electrical connections between the new electrodes and the fixed measurement devices. In this way, the cleaning or replacement of electrodes requires the carrying out of a very complex process.

Moreover, electrochemical detection devices sometimes give rise to bubbles in the test solution that remain in the solution as the solution flows through the cell. The bubble that remain in the test solution are deformed elastically when pressure is applied to the test solution. These elastic deformations of the bubbles give rise to noise at the time of measurement, and measurements cannot be made with accuracy.

SUMMARY OF THE INVENTION

The electrochemical detection device of this invention, which overcomes the above-discussed and numerous other disadvantages and deficiencies of the prior art, comprises a cell unit that has a cell therein and a supporter that rotatably supports said cell unit and that is made in one piece with said cell unit, wherein said cell unit has a cell block that has a test solution introduction route through which a test solution flows after being introduced into the inside of said cell block and that has a test solution outlet route through which the test solution leaves the inside and that has a reference electrode and a counter electrode provided so that they come into contact with the test solution flowing from said test solution introduction route to said test solution outlet route; a gasket that has an opening constituting said cell, and that is in contact with said cell block so that said opening is connected with both the test solution introduction route and the test solution outlet route; a working electrode that is in contact with said gasket so that the electrode surface of said working electrode faces and opening of the gasket, and said supporter has a pressure means that pushes said working electrode onto said cell block by means of said gasket while said supporter and said cell unit are being incorporated into one piece, which removes the pressure from said pressure means.

In a preferred embodiment, the test solution introduction route of said cell block is disposed so as to be approximately horizontal and is connected with the opening of the gasket constituting said cell.

In a preferred embodiment, the test solution outlet route of said cell block is connected with the opening of said gasket constituting said cell via a slit that is level in the horizontal direction. The test solution outlet route passes through the inside of said cell block in an almost perpendicular fashion, to connect with said slit. The counter electrode is placed in a hole for the introduction of the counter electrode so as to be installed into the cell block, and said hole for the introduction of the counter electrode is almost parallel with the test solution introduction route and is connected with the test solution outlet route. The reference electrode is placed in a hole for the introduction of the reference electrode so as to be installed into the cell block, and said hole for the introduction of the reference electrode is at about right angles to both the test solution outlet route and the hole for the introduction of the counter electrode and is connected with said test solution outlet route.

In a preferred embodiment, the gasket and the working electrode of said cell unit can be separated from said cell unit. The gasket and the working electrode can be separated from the cell block when the cell unit is rotated to separate from the supporter.

In a preferred embodiment, the cell unit and said supporter are fastened together by a stopping pin so as to be incorporated into one piece.

In a preferred embodiment, the pressure means pushes against the working electrode by means of an electrode-pushing plate. The pressure means has a ball and a spring, said ball pushing against said electrode-pushing plate by means of said spring. The ball and the spring of said pressure means can be brought close to and far from the electrode-pushing plate in a unified manner by means of a cam mechanism. An operation level for said cam mechanism is disposed on said supporter. The electrode-pushing plate has a conductive electrode-contact plate, which comes into contact with said working electrode, and a lining metal layer, which comes into contact with said ball.

Thus, the invention described herein makes possible the objectives of (1) providing an electrochemical detection device that can have its cell cleaned readily, because the cell can easily be opened; (2) providing an electrochemical detection device that can readily be reassembled after the cell has been opened; (3) providing an electrochemical detection device the working electrode of the can readily be removed and replaced; (4) providing an electrochemical detection device in which the contact efficiency of the electrode surface of the working electrode and the test solution is high, so that the accuracy of measurements is excellent; (5) providing an electrochemical detection device in which the working electrode is disposed so as to close the opening of the cell and is uniformly pushed against the cell, so that the said working electrode can seal the cell with assurance, thereby preventing solutions from leaking out of the cell; and (6) providing an electrochemical detection device in which even if bubbles are formed in the sample solution within the cell or elsewhere, measurements can be carried out without the influence of noise arising from the bubbles, and accordingly the accuracy of measurement is excellent.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
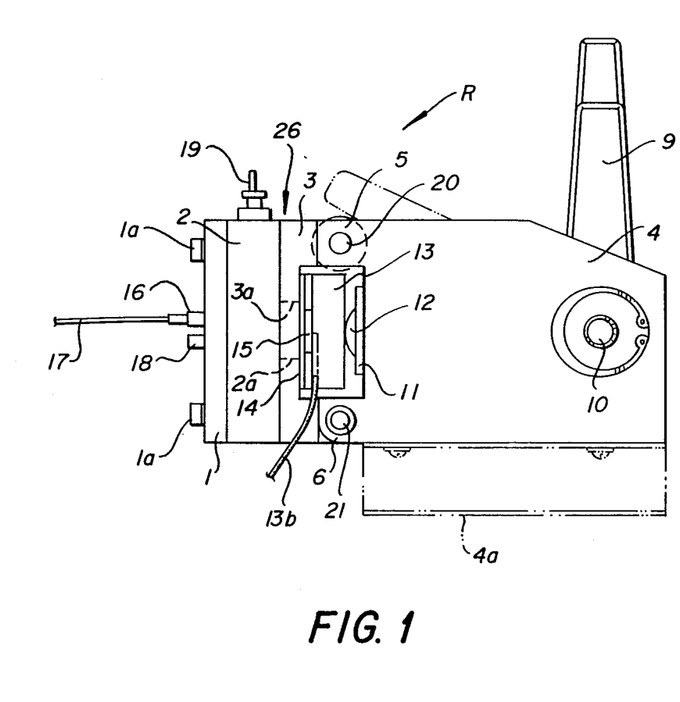
FIG. 1 is a side view showing an electrochemical detection device of this invention.
Figure 2:
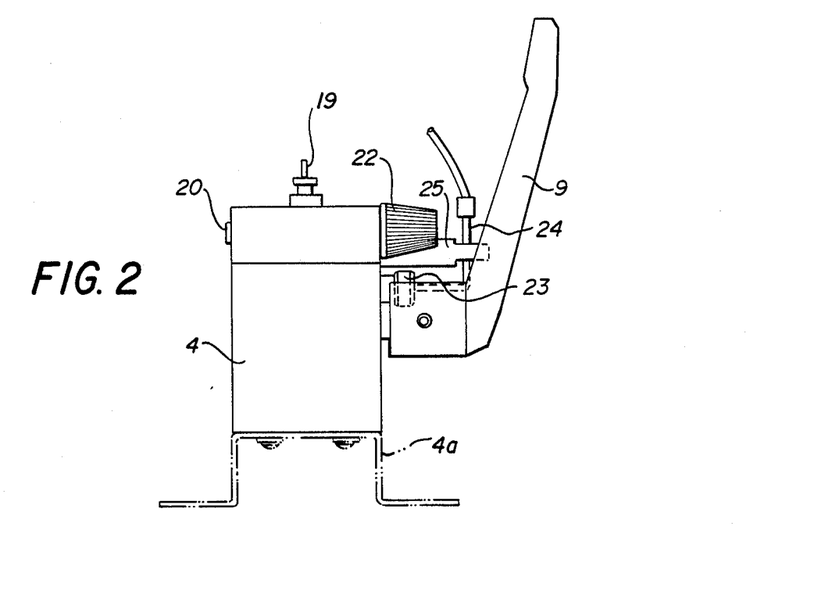
FIG. 2 is a back view showing the electrochemical detection device of this invention.
Figure 3:
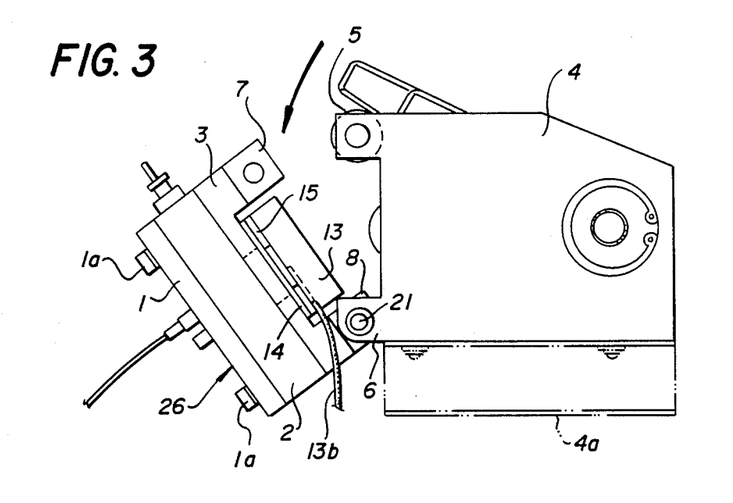
FIG. 3 is a side view showing the electrochemical detection device of this invention when the cell unit has been separated from the supporter.

The electrochemical detection device of this invention has, as shown in FIGS. 1-3, for example, a supporter 4 that is fixed on a stand 4a and a cell unit 26 that is rotatably supported by the supporter 4.

The cell unit 26 has a block support plate 3 supported so that it can be rotated up and down on the front surface of the supporter 4; a cell block 2 that is held on the front surface of the block support plate 3, the said cell block 2 being made from an appropriate synthetic resin material; and a block cover plate 1 fixed onto the front side of the said cell block 2. The block cover plate 1, the cell block 2, and the block support plate 3 are held together in one piece by, for example, screws 1a that are introduced from the block cover plate side.

The block support plate 3 has a circular opening 3a in its center, and a cylinder 2a that projects from the back central part of the cell block 2 into the opening 3a. The block support plate 3 has on its upper and lower parts projections 7 and 8 (see FIG. 3) projecting from the back surface (on the side of the supporter 4). At the upper and lower parts of the front surface of supporter 4 (on the side of cell unit 26), there are projections 5 and 6 that project toward the side of cell unit 26. The projection 6 at the bottom of supporter 4 annd the projection 8 at the bottom of the block supporter 3 are fastened together by a support pin 21 so that they can rotate. The projection 7 at the top of the block support plate 3 and the projection 5 at the top of the support plate 4 are fastened by a fastening pin 20. The fastening pin 20, when removed from the fastening of the projections 7 and 5, makes it possible for the entire cell unit 26 to rotate downward as shown in FIG. 3 around the support pin 21. The fastening pin 20 has, as shown in FIG. 2, a knob 22 that projects from the side of the supporter 4 when the projections 7 and 5 are fastened. The knob 22 is held when the fastening of projections 7 and 5 are released via fastening pin 20, removing the fastening pin 20 from projections 7 and 5.

Figure 4:
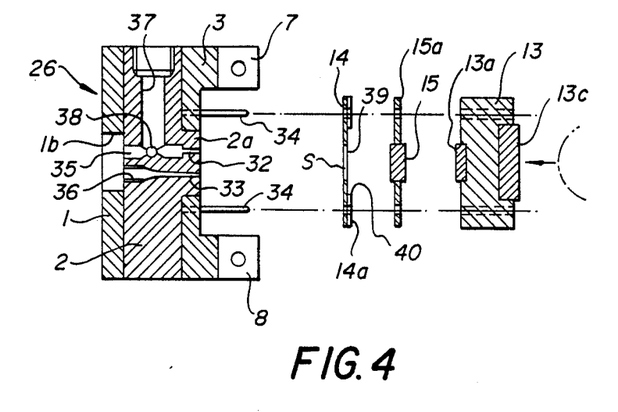
FIG. 4 is a sectional view showing the cell unit that has been decomposed.
Figure 6:
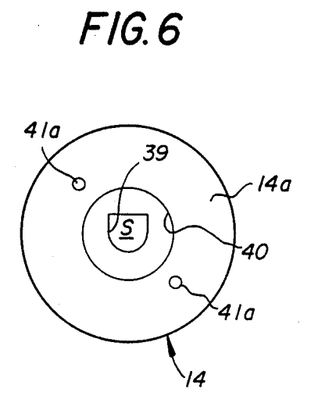
FIG. 6 is a back view showing the gasket.

There is a space between the projections 7 and 8 on the back surface of the block support plate 3 and the projections 5 and 6 on the front surface of the support 4. In this space, there is a gasket 14, which is, as shown in FIG. 4, supported on a pair of guide pins 34 that are on the block support plate 3. The guide pins 34 are provided in the block support plate 3 symmetrically around the center of opening 3a. The guide pins 34 extend from the block support plate 3 toward the supporter 4. The gasket 14 is made from, for example, a Teflon sheet, and, as shown in FIG. 6, it has a U-shaped opening 39 in its central part. On the side of supporter 4 of the said gasket 14, a ring-shaped reinforcement seal 14a is applied. The ring-shaped reinforcement seal 14a has an opening 40 in its central portion, which surrounds the central part of the U-shaped opening 39 of the gasket 14. The gasket 14 and the reinforced seal 14a have holes 41a through which the guide pins 34 pass.

The gasket 14 is supported by the pair of pins 34, and is pushed to meet both the end surface of the cylinder 2a of the cell block 2 (this end surface is fitted into the opening 3a of the center of the block support plate 3) and the back surface of the block support plate 3.

The guide pins 34, which support the gasket 14, support the support plate 15a that supports a working electrode 15 in its center. The support plate 15a has an opening in its central portion, and the working electrode 15 is fixed in the said opening. The said support plate 15a is made of plastic slightly thinner than working electrode 15 is. The electrode surface of the working electrode 15 is placed on the side of gasket 14. The said electrode surface is placed in the opening 40 of the reinforcement seal 14a that is applied to the gasket 14, and touches the edge of the opening 39 of the gasket 14. The opening 39 of the gasket 14 forms a cell S that is surrounded by the end surface of the cylinder 2a of the cell block 2 and the working electrode 15. Therefore, the size of the said cell S can be set by the size of the opening 39 of gasket 14 into the working electrode 15 pushed.

The pair of guide pins 34 that support the support plate 15a of the working electrode 15 support an electrode-pushing plate 13 made of plastic. The electrode-pushing plate 13 has a conductive metal electrode contact plate 13a opposite to working electrode 15. The electrode contact plate 13a projects slightly from the said electrode-pushing plate 13 toward the support plate 15. The electrode contact plate 13a is connected with a lead wire 13b, which is disposed along the electrode-pushing plate 13. In the central part of the back side of the said electrode-pushing plate 13, there is a lining metal layer 13c, which projects slightly from the back surface of the electrode-pushing plate 13. The said lining metal layer 13c touches at one point a ball 12 to be described later, and is pushed by the ball 12. When the lining metal layer 13c, is pushed by the ball 12, the electrode contact plate 13a is pushed against the working electrode 15. In this way, the working electrode 15 and the electrode contact plate 13a are connected electrically. The lead wire 13b is connected with a fixed measurement device on the outside, and sends electrical signals from the working electrode 15 to the measurement device.

Figure 5:
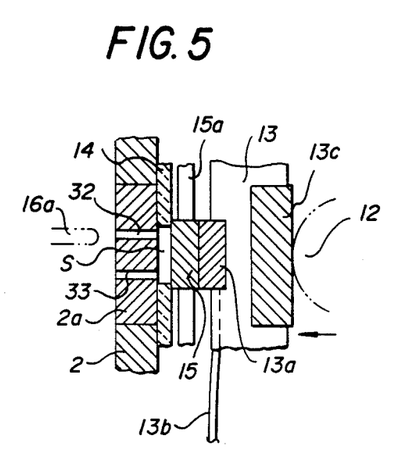
FIG. 5 is a sectional view showing one part of the cell unit.

Inside the cell block 2 of the cell unit 26, there are provided a hole 35 for the introduction of the counter electrode and a route 36 for the introduction of the test sample. One end of the hole 35 for the introduction of the counter electrode faces an opening 1b that is formed in the central part of the block cover plate 1. The other end of the hole 35 for the introduction of the counter electrode is connected with the cell S that is formed in the opening 39 of the gasket 14 via a slit 32. The slit 32 is level in the horizontal direction, and passes through the cylinder 2a of the cell block 2. The leading end 16a of a counter electrode 16 (see FIG. 5) is introduced through the hole 35 for the introduction of the counter electrode 16, and faces the cell S when passed through the slit 32.

The route 36 for the introduction of the sample solution is provided at the bottom of the hole 35 for the introduction of the counter electrode 16. One end of the route 36 for the introduction of sample solution faces the opening 1b of the block cover plate 1. The said one end is provided with a connector 18 (see FIG. 1) so that the said route 36 for the introduction of sample solution is connected with a tube through which the sample solution flows. The other end of the route 36 for the introduction of sample solution is connected with the cell S through a small hole 33 that pierces the cylinder 2a of the cell block 2. The diameter of the route 36 for the introduction of sample solution decreases stepwise toward the cell S. In the inside of the route 36 for the introduction of sample solution, sample solution flows and passes through the small hole 33 to enter cell S. The test solution that flows into the cell S is dispersed upward inside the cell S, to pass through the slit 32 and flow into the hole 35 for the introduction of the counter electrode.

Figure 7:
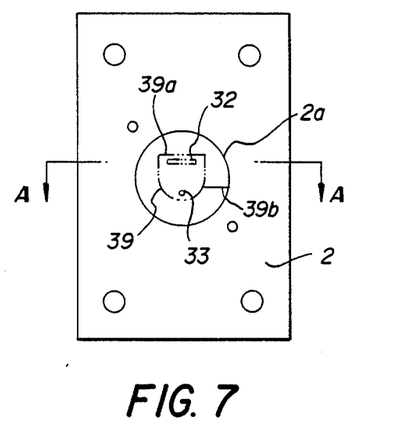
FIG. 7 is a back view showing the cell block.

The slit 32 and the small hole 33 that pierce the cylinder 2a of the cell block 2, as shown in FIG. 7, face the opening 39 that is U-shaped in cross-section of the gasket 14 that forms cell S. The slit 32 faces a position slightly below the horizontal upper edge 39a of the opening 39 of the gasket 19. The small hole 33 faces a position slightly above the U-shaped lower edge 39b of the opening 39 of the gasket 14. In the cell block 2, as shown in FIG. 4, there is formed an outlet route 37 for sample solution, extending upward from the central part of the hole 35 for the introduction of the counter electrode. The outlet route 37 for sample solution is connected at its lower end with the hole 35 for the introduction of the counter electrode, and its upper end opens above the upper surface of the cell block 2. At the upper end of the said outlet route 37 for sample solution, there is provided a connector 19 (see FIG. 1) for the purpose of connecting the tube in which the sample solution flows with the said outlet route 37 for sample solution.

Figure 8:
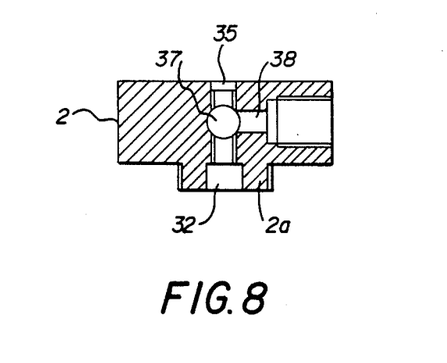
FIG. 8 is a sectional view along line A—A of FIG. 7.

Inside the cell block 2, as shown in FIG. 8, there is formed a hole 38 for the introduction of the reference electrode, which extends upward from the center part of the hole 35 for the introduction of the counter electrode. One end of the hole 38 for the introduction of the reference electrode opens from the side of the cell block 2. The said hole 38 for the introduction of the reference electrode, at this opening end, is provided with an electrode connector 23 that projects from the side of the cell block 2, as shown in FIG. 2. The said electrode connector 23 is connected with the reference electrode, which is introduced into the hole 38 for the introduction of the reference electrode. At the upper part of the said electrode-connector 23, there is an electrode supporter 25. The electrode supporter 25 projects almost horizontally from the side of the cell block 2. The electrode supporter 25 immovably supports the reference electrode 24 that is connected with the electrode connector 23.

A pressure device is provided inside the supporter 4 that rotatably supports the cell unit 26. The pressure device fastens the cell unit 26 to the supporter 4 by the fastening pins 20, and when the cell unit 2 and the supporter 4 are fastened together, the working electrode 15 and the gasket 14 of the cell unit 26 can be pushed onto the cell block 2. Also, when the cell unit 2 and supporter 4 are fastened together, it is possible to withdraw the pressure of the working electrode 15 and the gasket 14 onto cell block 2.

Figure 9:
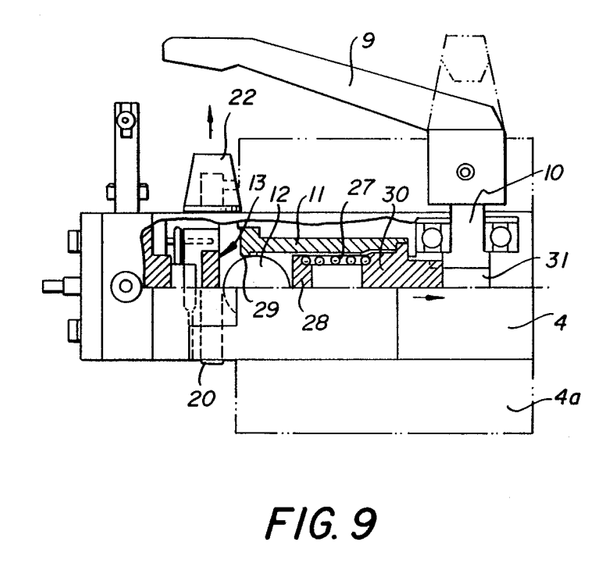
FIG. 9 is a partial sectional view showing the electrochemical detection device of this invention.

The said pressure device has a sleeve 11, as shown in FIG. 9. The sleeve 11 is disposed within the supporter 4 in a horizontal way so that one end thereof faces the electrode-pushing plate 13 of the cell unit 26. At the inside surface of the end of the said sleeve 11 on the side of the cell unit 26, there is a stopper 29 that projects to the inside, and there is a ball 12 made of metal on the inside of that end. The ball 12 is stopped on the stopper 29 of the sleeve 11 so as not to fly out of the sleeve 11. On the inside of the other end of the sleeve 11, there is fitted a cam folllower 30. One part of the cam follower 30 extends from the sleeve 11 toward the outside, and the said extension comes into contact with a cam 31. The cam 31 has attached a cam shaft 10 thereto so as to be at right angles to the sleeve 11. The cam shaft 10 is rotatably supported by the supporter 4. One end of the cam shaft 10 extends to the outside of the side of supporter 4, and a working level 9 is attached to the said extension. The working lever 9 rotates so as to rotate the cam 31 together therewith, and the sleeve 11 is moved along the axis of the said sleeve 11.

There is a spring 27 inside of the sleeve 11. The spring 27 fits at one end into the cam follower 30. The other end of the spring 27 fits into a stand 28, which is made to come into contact with the ball 12 via the pressure of the spring 27. Thus, the ball 12 is moved outward a fixed amount from the end surface of the sleeve 11 by the pressure of the spring 27.

The cell unit 26, which is provided with the cell block 2, the gasket 14, the working electrode 15, etc., rotates around the support pin 21, and is stopped by the stopping pin 20 of the supporter 4. In this way, the cell block 2 and the supporter 4 are fastened together. In this situation, the working level 9 if at a perpendicular position, as shown in FIGS. 1 and 2, moves the sleeve 11 inside the supporter 4 in the direction of the cell unit 26 by means of a cam mechanism. Together with the movement of the sleeve 11, the spring 27 inside the said sleeve 11 also moves. As a result, the ball 12 that is provided at the end of the said sleeve 11 pushes against the lining metal plate 13c of the electrode-pushing plate 13 in the direction of the cell block 2. Accordingly, the electrode contact plate 13a that is provided on the electrode-pushing plate 13 pushes the working electrode 15 and the gasket 14 gradually in the direction of the cell block 1. The ball 12 is in contact with the electrode-pushing plate 13 at one point, so it uniformly pushes the entire area of the said electrode-pushing plate 13. In this way, the edge of the opening 39 of the gasket 14 seals the space between the cell block 2 and the working electrode 15. Also, the electrode surface of the working electrode 15 comes to face the opening 39 of the gasket 14.

In these circumstances, the counter electrode 16 is introduced into the hole 35 for the introduction of the counter electrode in the cell block 2, and moreover, the reference electrode 24 is introduced into the hole 38 for the introduction of the reference electrode, so that sample solution can flow through the route 36 for the introduction of the test solution. The test solution that flows in the inside of the route 36 for the introduction of test solution passes through hole 33, and flows inside the cell S formed in the opening 39 of the gasket 14. The test solution that flows inside the cell S is dispersed through the cell S so as to fill it. At this time, since the opening 39 of the gasket 14 that forms the cell S is facing the electrode surface of the working electrode 15, the test solution inside the cell S comes into contact efficiently with the electrode surface of the said working electrode 15. The said test solution flows into the outlet route 37 for the removal of test solution via the slit 32. The working electrode 15 has a fixed difference in electrical potential from the tip 16a of the counter electrode 16 provided in the cell block 2, so a fixed voltage is applied to the test solution inside the cell S. In this way, the said test solution undergoes an electrochemical reaction. The changes in the electrical current based on those electrochemical reactions are then sent to the outside measurement devices by means of the lead wire 13b that is connected to the working electrode 15. Then, the amounts of specific substances in the test solution are measured by the said measurement devices.

During such measurement, bubbles may form and remain in the test solution that is in the cell S and elsewhere. Such bubbles are deformed elastically by the application of pressure to the test solution, and become noise at the time of making measurements. However, because there is a level slit 32 in the horizontal direction in the upper part of the inside of cell S, bubbles that form in the test solution in the cell S pass the said slit 32, and come to the surface rapidly in the outlet route 37 for the removal of test solution, which is almost perpendicular. As a result, at the time of measurement, it is possible to prevent completely any effect of the noise that might arise from such bubbles.

When the insides of the cell S, the working electrode 15, etc., are to be cleaned, or when the working electrode 15 is to be replaced, the working level 9 of the supporter 4 is moved in the direction shown by arrow R in FIG. 1. In this way, the sleeve 11 inside the supporter 4 is moved in the direction away from the cell unit 26, and the ball 12, which is in one piece with sleeve 11, is separated from the electrode-pushing plate 13. Therefore, said electrode-pushing plate 13 removes pressure from working electrode 15, and the cell unit 26 receives no pressure from the pressure device. As a result, pressure is not applied to the stopping pin 20 that is fastened in the space between the cell unit 26 and the supporter 4, and the said stopping pin 20 can readily be removed from the cell unit 26 and the supporter 4.

When the stopper pin 20 is removed from the supporter 4 and the cell unit 26, the cell unit 26 rotates in the direction shown by arrow A in FIG. 3 around the support pin 21. Because the supporter 4 is fixed on the stand 4a, the cell unit 26 rotates without hindrance in a position lower than the bottom of the supporter 4. Then, while the cell unit 26 is rotating around the support pin 21, the electrode-pushing plate 13, the working electrode 15, and the gasket 14 are removed from the guide pins 34 provided in the block holding plate 3, and each can be separated from the cell block 2. Also, the counter electrode 16 and the reference electrode 24 provided in the cell block 2 can be removed from the cell block 2, and the working electrode 15, the route 36 for the introduction of test solution of the cell block 2, the outlet route 37 for test solution, etc., can be cleaned. Even when the working electrode 15 is to be replaced, in the same way, the electrode-pushing plate 13 can be removed from the guide pins 34, and the working electrode 15 can be removed from the cell block 2, so that it is possible to fit another working electrode 15 to the guide pins 34.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. An electrochemical detection device comprising as one piece, a cell unit and a supporter; said cell unit comprising a cell block, gasket and working electrode, wherein said cell block contains a test solution introduction means and a test solution outlet means having a test solution outlet route both being substantially normal to the working electrode, through which the test solution flows following introduction thereof into the cell block, and reference and counter electrodes adapted to be in contact with said test solution after introduction thereof, said gasket containing an opening defining the cell which communicates with the test solution introduction and outlet means and communicating with the working electrode; said supporter containing a pressure means adapted to push the working electrode first against the gasket and then onto the cell block, and also adapted to retract the working electrode from the cell block, wherein said pressure means comprises a ball, a spring inside a sleeve horizontally disposed within said supporter, and an electrode-pushing plate disposed between the ball and the working electrode whereby upon movement of the ball, the electrode-pushing plate comes into contact with said working electrode.

2. An electrochemical detection device according to claim 1, wherein the test solution outlet route of said cell block is connected with the opening of said gasket constituting said cell via a slit that is level in the horizontal direction.

3. An electrochemical detection device according to claim 2, wherein said test solution outlet route passes through the inside of said cell block in an almost perpendicular fashion, to connect with said slit.

4. An electrochemical detection device according to claim 3, wherein said reference electrode is placed in a hole for the introduction of the reference electrode so as to be installed into the cell block, and said hole for the introduction of the reference electrode is at about right angles to both the test solution outlet route and the hole for the introduction of the counter electrode and is connected with said test solution outlet route.

5. An electrochemical detection device according to claim 1, wherein the gasket and the working electrode can be separated from the cell block, when the cell unit is rotated to separate from the supporter.

6. An electrochemical detection device according to claim 1, wherein said cell unit and said supporter are fastened together by a stopping pin so as to be incorporated into one piece.

7. An electrochemical detection according to claim 1, wherein said electrode-pushing plate has a conductive electrode-contact plate, which comes into contact with said working electrode, and a lining metal layer which comes into contact with said ball.

8. An electrochemical detection device as claimed in claim 1, wherein the ball is brought into contact and out of contact with the electrode-pushing plate by means of a cam mechanism having an operation lever disposed on said supporter.

9. An electrochemical detection device according to claim 8, wherein an operation lever for said cam mechanism is disposed on said supporter.

* * * * *